United States Patent
Duvvuri et al.

[11] Patent Number: 5,972,955
[45] Date of Patent: Oct. 26, 1999

[54] WATER SOLUBLE C-RING ANALOGUES OF 20(S)-CAMPTOTHECIN

[75] Inventors: Subrahmanyam Duvvuri; Venkateswarlu Akella; Sharma Manohara Vedula; Archana Prabhakar Kulakarni, all of Andhra Pradesh, India

[73] Assignee: Dr. Reddy's Research Foundation, Hyderabad, India

[21] Appl. No.: 08/771,390

[22] Filed: Dec. 19, 1996

Related U.S. Application Data

[63] Continuation-in-part of application No. 08/655,259, Jun. 5, 1996, abandoned, and a continuation-in-part of application No. 08/471,640, Jun. 6, 1995.

[51] Int. Cl.$^6$ ........................ A61K 31/47; C07D 491/147
[52] U.S. Cl. ............................................. 514/283; 546/48
[58] Field of Search .............................. 546/48; 514/283

[56] References Cited

U.S. PATENT DOCUMENTS

| | | | |
|---|---|---|---|
| 4,399,282 | 8/1983 | Miyasaka | 546/48 |
| 4,473,692 | 9/1984 | Miyasaka | 546/48 |
| 4,513,138 | 4/1985 | Miyasaka | 546/48 |
| 4,545,880 | 10/1985 | Miyasaka | 204/158 |
| 4,604,463 | 8/1986 | Miyasaka | 544/125 |
| 4,981,968 | 1/1991 | Wall | 544/361 |
| 5,053,512 | 10/1991 | Wani | 546/48 |
| 5,122,526 | 6/1992 | Wall | 514/253 |
| 5,391,745 | 2/1995 | Danishefsky | 546/48 |
| 5,446,047 | 8/1995 | Danishefsky | 514/280 |
| 5,468,754 | 11/1995 | Hausheer | 514/283 |
| 5,525,731 | 6/1996 | Danishefsky | 546/48 |
| 5,541,327 | 7/1996 | Danishefsky et al. | 546/48 |

FOREIGN PATENT DOCUMENTS

| | | |
|---|---|---|
| 58-154584 | 9/1983 | Japan . |
| 9746562 | 4/1997 | WIPO . |
| 9746563 | 4/1997 | WIPO . |
| 9746564 | 4/1997 | WIPO . |

OTHER PUBLICATIONS

Chemical Abstracts vol. 100, No. 7, Feb. 13, 1984, Abstract No. 51876f JP 58 154 584A (Yakult Co.).
Biochemical Pharmacology, vol. 34, No. 8, Apr. 15, 1985, Masako Fukada, et al. pp. 1225–1230.
Database WPI-AN92-71412E XP002034966 JP 57116074A (Yakult Honska K.K.) Jul. 19, 1982.
Chemical Abstracts vol. 100, No. 11, Mar. 12, 1984, Abstract No. 85671a JP 58–154 583A (Yakult Co.).
Chem. Pharm. Bull., vol. 39, 3183 (1991), Sawada et al.
J. Org. Chem., vol. 60, 5739–5740 (1995), Wood et al.
Chem. Pharm. Bull., vol. 41, 971–974 (1993),. Yaegishi et al.
J. Med. Chem., 29, 2358–2363 (1986), M.C. Wani et al.
J. Org. Chem., 59, 7033–7037 (1994), L. Snyder et al.
Chem. Pharm. Bull., 40(3), 683–688 (1992), A. Ejima et al.
Chem. Pharm. Bull., 41 (2), 310–313 (1993), S. Sawada et al.
Chem. Pharm. Bull., 39, No. 10 pp. 2574–2580 (1991), S. Sawada et al.
J. Med. Chem., 34, 98–107 (1991), W.D. Kingsbury et al.
J. Biol. Chem., 260, 14873–14877 (1985), Y.H. Hsiang et al.
J. Med. Chem., 36, 2689–2700 (1993), M.E. Wall et al.
J. Med. Chem., 32, 715–720 (1989), L.P. Hertzberg et al.
J. Med. Chem., 37, 40–46 (1994), T.G. Burke et al.
Ind. J. Chem., 10(B), 453–454 (1972), T.R. Govindachary et al.
Chem. Pharm. Bull, Japan 39(10), 1446–1454 (1991), S. Sawada e.

*Primary Examiner*—Alan L. Rotman
*Assistant Examiner*—Charanjit S. Aulakh
*Attorney, Agent, or Firm*—Ladas & Parry

[57] ABSTRACT

Novel water soluble C-ring analogs of 20(S)-camptothecin having the formula 1.

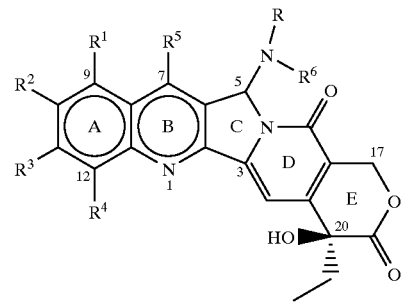

The compounds of the formula 1 are prepared from the compounds of the formula 12 having C-20(S) chiral carbon. The compounds of the formula 1 possess potent anti-cancer and anti-viral properties.

19 Claims, No Drawings

WATER SOLUBLE C-RING ANALOGUES OF 20(S)-CAMPTOTHECIN

This application is a continuation-in-part of copending application Ser. No. 08/655,259 filed on Jun. 5, 1996 and Ser. No. 08/471,640 filed Jun. 6, 1995.

The present invention relates to novel water soluble C-ring analogues of 20(S)-Camptothecin having the general formula 1.

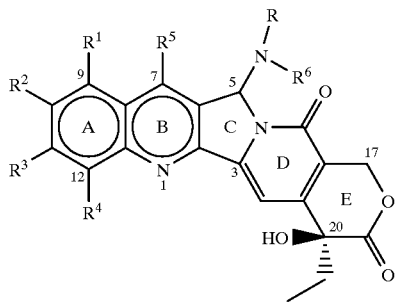

In the above formula 1, $R^1$, $R^2$, $R^3$ and $R^4$ are independently the same or different and represent hydrogen, hydroxy, lower alkoxy, aryloxy, lower alkanoyl, nitro, cyano, halo, carboxy, carbonyloxy, amino, substituted amino, lower alkyl, substituted lower alkyl or $R^2$ and $R^3$ combined together represent —O—$(CH_2)_n$—O— where n=1 or 2; $R^5$ represents hydrogen, lower alkyl, substituted lower alkyl, lower aralkyl, hydroxymethyl, carboxymethyl, aminomethyl, substituted aminomethyl where the amino group is mono or disubstituted in which both substituents are independent or combined together to form 5 or 6 membered cyclic ring system containing carbon and optionally containing one or two heteroatoms selected from, oxygen, nitrogen and sulfur, the number of atoms in the cyclic ring system is 5 or 6. R represents hydrogen, lower alkyl, lower alkenyl, lower alkanoyl, substituted lower alkyl, substituted lower alkanoyl, substituted lower alkenyl, lower alkoxycarbonyl, phenyl, benzyl or benzoyl in which the phenyl group may be unsubstituted or substituted; and $R^6$ represents hydrogen, hydroxy, lower alkoxy or COOR' where R' represents hydrogen, lower alkyl or lower aralkyl; $R^6$ may also represent amide or amino group in which the amide or the amino group can be unsubstituted, or mono or disubstituted in which both substituents are independent or combined together to form a cyclic ring system of 3 to 8 atoms containing carbon and optionally contains one or two heteroatoms selected from, nitrogen, oxygen and sulfur, the number of atoms in the cyclic ring system is 3 to 8 atoms; phenoxy, phenyl, benzoyl or benzyl where the phenyl group can be unsubstituted or substituted with mono, di or trisubstituents which may be selected from halogen, hydroxy, lower alkoxy, cyano, carboxy, nitro, amido, amino or substituted amino, lower alkyl, substituted lower alkyl; cycloalkyl or cycloalkyl lower alkyl where the cyclic ring is in the range of 3 membered to 7 membered ring system containing all carbon atoms; lower alkyl substituted with heterocyclic rings where the heterocyclic ring system having 3 to 7 atoms containing carbon with at least one heteroatom such as oxygen, nitrogen or sulfur, the number of atoms in the heterocyclic ring system being 3 to 7; lower alkanoyl; lower alkyl; substituted lower alkyl where the substituents can be halogen, hydroxy, alkoxy, aryloxy, carboxyl, cyano, thio, thioalkyl, thioaryl, aryl, heteroaryl, nitro, amido or amino in which amino group can be unsubstituted, mono, or disubstituted in which both substituents are independent or combined together to form a cyclic ring system of 3 to 8 atoms, the cyclic system containing carbon and optionally contains one or two heteroatoms selected from nitrogen, oxygen and sulfur;

All these compounds of the formula 1 are prepared from the compounds of the general formula 12 having C-20(S) chiral carbon,

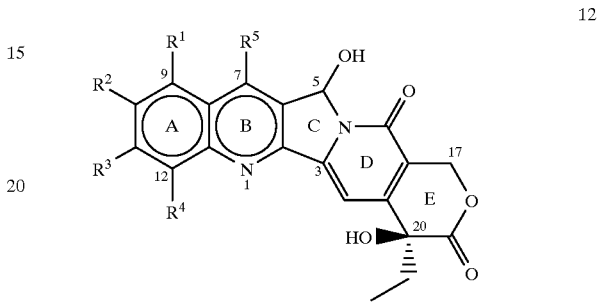

where $R^1$ to $R^5$ have the meaning described above.

20(S)-Camptothecin having the formula 2 is an alkaloid possessing strong antitumor activity.

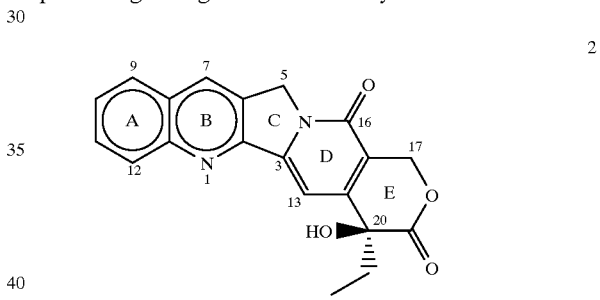

It was first isolated from the plant Camptotheca acuminata by Wall and co-workers in 1966. However, its development as a potential drug for cancer treatment has been abandoned due to unacceptable side effects on humans and due to its low water solubility as well as high toxicity problems. Since the discovery of its mechanism of action as an inhibitor of topoisomerise I by Liu and co-workers in 1985 [L. F. Liu, et al., *JBiol. Chem.* 260, 14873 (1985)], the research interest on camptothecin has once again taken momentum.

To overcome the problem of low water solubility and high toxicity of camptothecin, over the last 30 years, several research groups all over the world have prepared and investigated a number of camptothecin analogues involving the modification of rings A–E or the introduction of a variety of substituents on all the five rings of camptothecin of the formula 2 [M. E. Wall et al.,*J. Med. Chem.*, 36, 2689 (1993); R. P. Hertzberg et al., *J. Med. Chem.*, 715 (1989); S. W. Sawada et al., *Chem. Pharm. Bull*, 41(2), 310 (1993)]. Among the various camptothecin analogues prepared to date, only two of them namely, CPT-11 having the formula 3 [*Chem. Pharm. Bull.*, 39, 1446 (1991)],

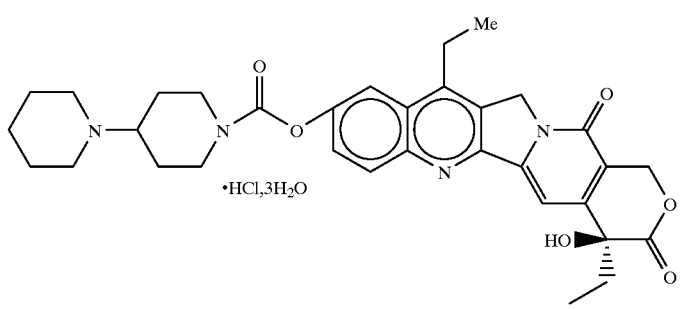

3

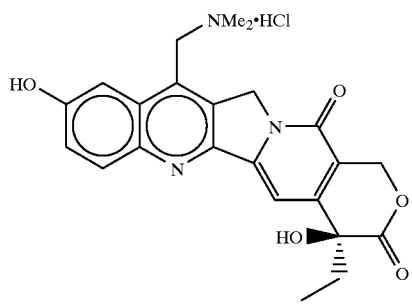

topotecan of the formula 4 [*J. Med. Chem.*, 34, 98(1991)]

4 were introduced as anti-cancer drugs in the market recently. Another compound namely, 9-aminocamptothecin of the formula 5 [*J. Med. Chem.*, 29 2358 (1986)],

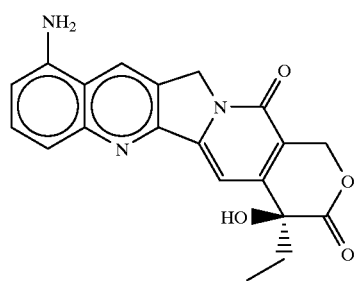

is currently undergoing phase III clinical trials. The extensively studied Structure-Activity Relationship (SAR) on camptothecin of the formula 2 [M. E. Wall et al., *J. Med. Chem.*, 36, 2689 (1993)] has revealed that 20(S)-α-hydroxy-δ-lactone (E-ring) moiety in camptothecin is essential for its activity. However, according to recent reports by Ejima et.al., replacement of hydroxyl group with a amino group at C-20 position leading to a compound such as 7-ethyl-10-methoxycamptothecin derivative of the formula 6[A. Ejima etal., *Chem. Pharm. Bull.*, 40(3), 683 (1992)],

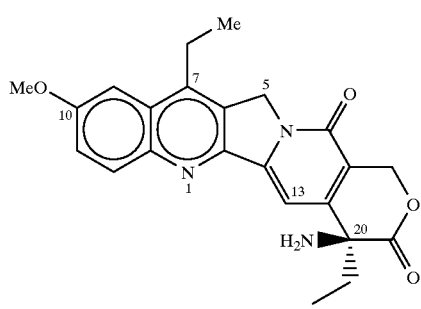

6

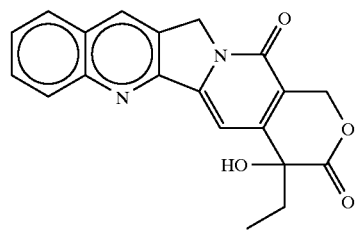

7 exhibited an increased in vivo antitumor activity than 20(RS)-camptothecin of the formula 7. Also in another report [Lawrence Snyder et.al., *J. Org. Chem.*, 59, 7033 (1994)], the 18-noranhydrocamptothecin analogue of the formula 8,

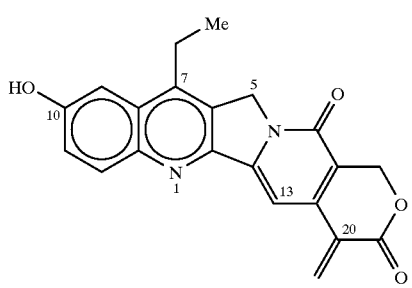

8 exhibited potent camptothecin like inhibition of topoisomerase I activity. Both these reports are contrary to the assumption that 20(S)-α-hydroxy functionality in camptothecin is an essential feature for its biological activity.

Based on the structure-activity results obtained for the camptothecin analogues prepared in the literature, it was established that the modification of substituents at C-9 and C-7 position of camptothecin of the formula 2 plays an important role in the enhancement of anticancer activity by imparting stability to the E-ring lactone [T. G. Burke etal., *J. Med. Chem* 37, 40(1994)]. It has also been recognized that the open form of the lactone moiety, namely, 'the Carboxylate form' is less effective therapeutically than the closed 'Lactone form' [Hertzberg et al., *J. Med. Chem.,* 32, 715 (1989); J. M. Covey, C. Jaxel et al., *Cancer Research.,* 49, 5016 (1989); Giovanella et al., *Cancer Research.,* 51, 3052 (1991)]. The recent studies by T. G. Burke et al., on the stability of 'closed lactone form' of various camptothecin analogues in the presence of protein called 'Human Serum Albumin' (HSA) indicated that the compounds such as CPT-11 of the formula 3 and 7-ethyl-10-hydroxycamptothecin (SN-38) of the formula 9

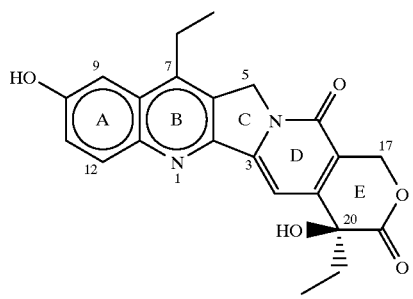

and Topotecan of the formula 4, in the presence of HSA at 37° C., exhibited a higher percentage (%) of lactone form at equilibrium than 20(S) camptothecin of the formula 2 and 9-aminocamptothecin of the formula 5 [T. G. Burke and Zihou Mi., *J. Med. Chem.,* 37 40 (1994); ibid., *Biochemistry.,* 33, 12540(1994)]. Based on these studies, it was recognized that the understanding of the factors influencing the lactone-carboxylate equilibrium of camptothecm analogues became an important determinant in the design of novel and therapeutically efficacious drug candidates in the camptothecin series.

Although the modification of substituents on rings A and B of camptothecin was taken up at a rapid pace to generate novel CPT analogues, ring 'C' analogues of camptothecins were limited presumably because of the research work carried out by Sawada et al., which claimed that the substituents at C-5 position of camptothecin has resulted in the reduction of anti-tumor activity of camptothecins and produced inactive analogues [Sawada S. et.al., *Chem. Pharm. Bull.,* 39(10), 2574(1991)]. The C-5 substituted camptothecins claimed by Sawada et al., (JP 58,154,584; U.S. Pat. No. 4,513,138; U.S. Pat. No. 4,473,692; U.S. Pat. No. 4,545,880; and U.S. Pat. No. 4,339,282) have the structural formula 10,

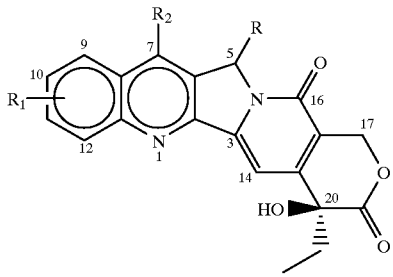

where R represents hydroxy, lower alkyl, lower alkoxy or acyloxy, $R^1$ represents hydrogen, methoxy at 9th position; hydrogen, hydroxy, lower alkoxy, acyloxy, SH, thioalkyl, thioacyl, nitro, amino, alkylamino, acylamino or halogen at 10th position and $R^2$ represents hydrogen, lower alkyl, lower aralkyl, $CH_2OH$, COOH, COOMe, $CH_2OR'$ where R' represents lower alkyl or acyl group.

The recent findings by K. H. Lee et al., [*Bio. Org. MedChem.Lett.,* 5(1), 77(1995)] which includes the preparation of 5-hydroxymethyl camptothecin by the reaction of formaldehyde in N,N-dimethylformamide and 4-piperidinopiperidine on 20(S)-camptothecin, has revealed the reduced anti-tumor activity of these compounds. Also, Danishefsky et al., prepared some of the C-5 substituted 20(RS)-camptothecin derivatives by a totally synthetic approach [U.S. Pat. No. 5,391,745 and U.S. Pat. No. 5,446,047].

However, the synthetically prepared 5-substituted camptothecin derivative of the formula 11 [Terasawa et. al., *Heterocycles,* 38,81(1994)] claimed to have anti-tumor activity comparable to that of 20(S)-camptothecin.

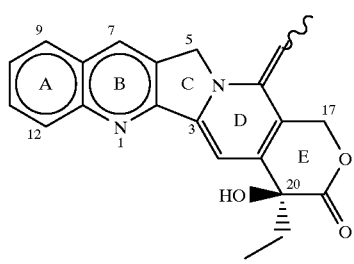

Keeping all these factors in mind, we focused our research studies on 20(S)-camptothecin aimed at the design of novel camptothecin analogues which can exhibit improved water solubility and improved stability of lactone form in solution. We identified an oxidative reaction in alcoholic solvents for this purpose. The resultant findings have culminated into the discovery of a novel synthetic transformation which can introduce a variety of alkoxy groups at C-5 position of 20(S)-camptothecins of the formula 14,

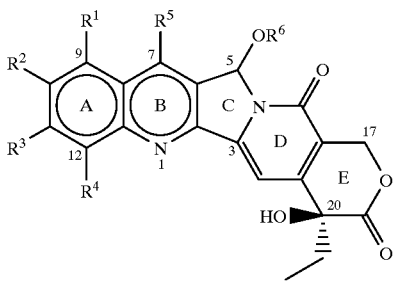

14 where $R^1$ through $R^6$ have the meaning described above, the subject matter of which was described in our pending application for patent bearing the Ser. No. 08/771,391.

There is provided a process for the preparation of the compounds of the formula 14,

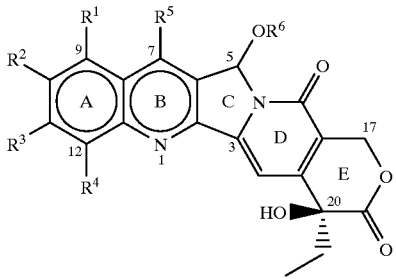

14 wherein $R^1$, $R^2$, $R^3$, $R^4$ are independently the same or different and represent hydrogen, hydroxy, aryloxy, lower alkoxy, lower alkanoyl, nitro, cyano, halo, carboxy, carbonyloxy, amino, substituted amino, lower alkyl, substituted lower alkyl or $R^2$, $R^3$ together represent —O—(CH$_2$)$_n$—O— where n=1 or 2; $R^5$ represents hydrogen, lower alkyl, substituted lower alkyl, lower aralkyl, hydroxymethyl, carboxymethyl, aminomethyl, substituted aminomethyl where the amino group may be mono or disubstituted in which both substituents are independent or combined together to form a cyclic ring system of a total of 5–6 atoms containing carbon and optionally one or two heteroatoms selected from oxygen, nitrogen or sulfur; and $R^6$ represents hydrogen; phenyl or benzyl where the phenyl group may be unsubstituted or substituted with mono, di or trisubstituents which may be selected from halogen, hydroxy, lower alkoxy, cyano, carboxyl, nitro, amino or substituted amino, lower alkyl, substituted lower alkyl; cycloalkyl or cycloalkyl lower alkyl where the cyclic ring is in the range of 3 membered to 7 membered ring system containing all carbon atoms; lower alkyl groups substituted with heterocyclic rings where the heterocyclic ring system has a total of 3 to 7 atoms, the ring system contains carbon with at least one heteroatom such as oxygen, nitrogen or sulfur; lower alkanoyl; benzoyl where the phenyl group can be unsubstituted or substituted; lower alkenyl; lower alkyl; substituted lower alkyl, substituted lower alkenyl or substituted lower alkanoyl where the substituents can be halogen, hydroxy, lower alkoxy, aryloxy, thio, thioalkyl, thioaryl, aryl or heteroaryl, carboxy, cyano, nitro, amido or amino in which the amino group can be unsubstituted or mono, or disubstituted in which both substituents are independent or combined together to form 5 or 6 membered cyclic ring system containing carbon, and optionally contains one or two heteroatoms selected from oxygen, nitrogen or sulfur, the total number of atoms in the cyclic ring system being 5 or 6; with the proviso that (i) when $R^1$ is methoxy group, $R^6$ is not hydrogen or lower alkyl group; (ii) when $R^2$ is hydroxy, lower alkoxy, thioalkyl, nitro, amino, alkylamino, acylamino, and halogen, $R^6$ is not hydrogen or lower alkyl group; (iii) when $R^5$ is lower alkyl, lower aralkyl, CH$_2$OH, COOH, COOMe, or CH$_2$OR" where R" represents lower alkyl or acyl group, $R^6$ is not hydrogen or lower alkyl group (iv) when $R^1$ is methoxy group, $R^2$ is hydroxy, lower alkoxy, thioalkyl, nitro, amino, alkylamino, acylamino, or halogen, $R^5$ is lower alkyl, lower aralkyl, CH$_2$OH, COOH, COOMe or CH$_2$OR" where R" represents lower alkyl or acyl group, $R^6$ is not hydrogen or lower alkyl group; (v) when $R^1$ through $R^5$ represent hydrogen, $R^6$ is not hydrogen or lower alkyl group, which comprises, (i) reacting the compounds of the formula 16,

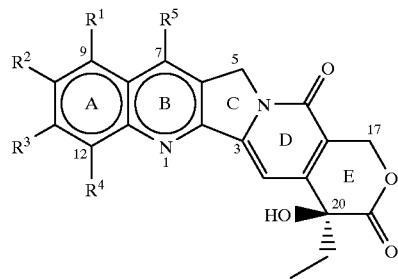

16 where $R^1$ to $R^5$ have the meaning described above, in the presence of an acid and an oxidizing agent which is a ferric salt, with a compound having the formula $R^6$—OH where $R^6$ represents lower alkyl, lower alkenyl, (C$_3$–C$_7$)cycloalkyl, haloalkyl or hydroxyalkyl, to obtain compounds of the formula 12 and compounds of the formula 17,

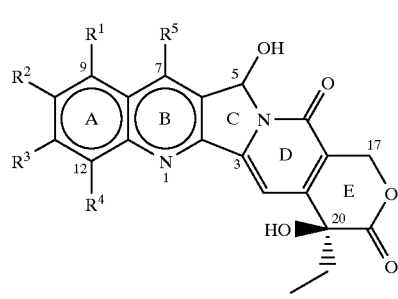

12

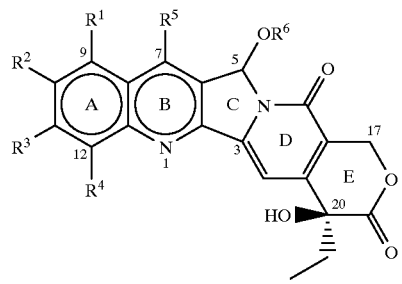

17 wherein $R^1$, $R^2$, $R^3$, $R^4$, $R^5$ have the meaning given above, (ii) separating the compounds of the formulae 12 and 17 prepared in the step (i), by conventional methods, (iii) hydrolyzing the compounds of the formula 17, by conventional methods, to obtain additional amounts of the compounds of the formula 12, (iv) reacting the compound of the formula 12, in the presence of an acid, with a compound having the formula $R^6$—OH to obtain compounds of the formula 14,

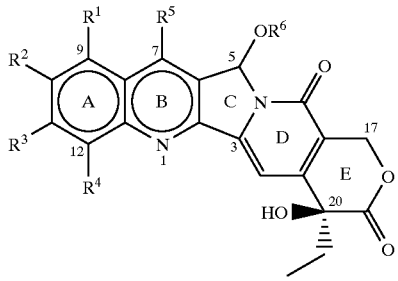

14 where $R^1$, $R^2$, $R^3$, $R^4$ and $R^5$ have the meaning described above and $R^6$ is as defined above.

Functional group transformation of these 5-alkoxy camptothecins of the formula 14 produced a large number of novel C-5-N-substituted 20(S)-camptothecin analogues of formula 1, which forms the subject matter of the present invention.

Hence, the discovery led to a facile and versatile semi-synthetic methodology by which virtually every camptothecin derivative known in the literature can be transformed into a variety of C-5 substituted camptothecin analogues. In another co-pending application for patent bearing Ser. No. 08/772,071, we have described and claimed the compounds of the formula 15,

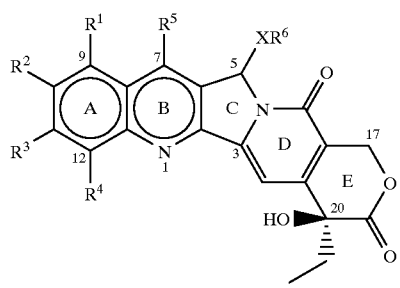

15 where X represents $CH_2$ or CHR groups.

Therefore, the present invention provides a novel process for the preparation of various C-5-N-substituted 20(S)-camptothecin derivatives of the formula 1 where $R^6$ has the meaning described above, starting from the compounds of the formula 12,

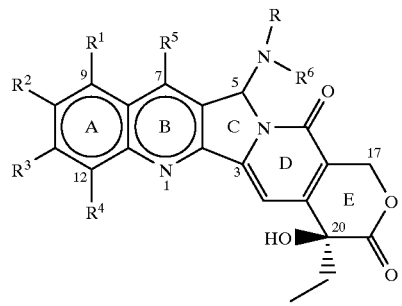

12 where $R^1$ through $R^6$ have the meaning described above. Furthermore, the vast variety of substituents represented by compounds of formula 1 have improved water solubility ranging from 1 mg to 15 mg per ml. All of the compounds prepared by the present invention exhibited significant in vitro anti-tumor activity against a wide range of human tumor cell lines.

DETAILED DESCRIPTION OF THE INVENTION

The present invention particularly provides C-5-N-substituted water soluble analogues of 20(S)-Camptothecin having the formula 1,

1 where R, $R^1$, $R^2$, $R^3$, $R^4$, $R^5$ and $R^6$ have the meaning described above. Throughout the present invention, the terms representing $R^1$ through $R^6$ in these compounds have the following definitions.

The term 'lower alkyl' denotes a univalent, branched or straight hydrocarbon chain containing 1 to 8 carbon atoms. Representative examples of the alkyl groups are methyl, ethyl, propyl, isopropyl, butyl, sec.butyl tert.butyl pentyl, iso pentyl, tert. pentyl, hexyl, isohexyl and octyl.

The term 'lower alkenyl' represents a branched or straight hydrocarbon chain having sp or $sp^2$ carbon centers containing 1 to 8 carbon atoms. Representative examples of the alkenyl groups are vinyl, propenyl, butenyl pentenyl, isopropenyl, isobutenyl, proparginyl, hexenyl and octenyl.

The term 'halogen' or 'halo' represents chlorine, bromine or fluorine. The term 'haloalkyl' denotes alkyl groups substituted with halogens, preferably fluorine, bromine or chlorine. Representative examples of the haloalkyl groups are chloroethyl, bromopropyl, fluoroethyl, trifluoroethyl, trichloroethyl and trifluorobutyl.

The term 'lower alkoxy' denotes lower alkyl groups as defined above attached via oxygen linkage to the rest of the molecule. Representative examples of these groups are methoxy, ethoxy, isopropoxy, tert.butoxy, hexoxy, heptoxy and octoxy.

The term 'lower alkanoyl' denotes lower alkyl or lower alkenyl groups as defined above attached via a carbonyl group to the rest of the molecule. Representative examples of these groups are acetyl, propionyl, propenoyl, crotanoyl, butanoyl, pentanoyl and isopentanoyl.

The term 'aminoalkyl' represents the lower alkyl groups as defined above substituted with amino groups. Representative examples of the aminoalkyl groups are 2-aminopropyl, 4-aminobutyl and 5-aminopentyl. The amino groups may also be mono or disubstituted and representative examples of these substituted amino groups are dimethylamino, diethylamino, dibenzylamino, ethylisopropylamino, pyrrolidino, piperidino, morphilino and piperzino.

The term 'heteroatom' refers to oxygen, nitrogen or sulfur. The term 'aryl or heteroaryl' represents groups of aromatic nature having 5 or 6 membered rings which may be selected from phenyl, biphenyl, naphthyl, pyridyl, quinoline, isoquinoline, indole, pyrol, furan, benzofuran, thiophene, pyramidine, piperizine, thiozolidine and imidazole.

The term 'substituted phenyl' group used in the present invention refers to those substituents which can be selected from groups such as hydroxyl, lower alkyl, haloalkyl, phenyl, benzyl, halogen, lower alkoxy, thioalkoxy, benzyloxy, carboxyl, cyano, nitro, amido, amino, and alkylamino. Examples of such groups are 4-hydroxyphenyl, 3-methoxyphenyl, 4-fluorophenyl, 4-trifluoromethylphenyl, N,N-dimethylaminophenyl, and 4-carbomethoxyphenyl.

The term 'substituted alkyl' group used in the present invention refers to those substituents which can be selected from groups such as hydroxyl, alkyl, haloalkyl, phenyl, benzyl, halogen, alkoxy, thioalkoxy, benzyloxy, carboxyl, carbonyloxy, cyano, nitro, amido, amino and alkylamino. Examples of such groups are fluoroethyl, chloropropyl, hydroxyethyl, methoxypropyl, N,N-diethylaminoethyl, N-benzoylaminopropyl, trifluoroethoxyethyl, phenoxyethyl, carbomethoxyethyl, (p-fluorobenzoyloxy)ethyl, aminopropyl, and 2-thioethyl.

The term 'substituted amino' group used in the present invention refers to those substituents which can be selected from groups such as hydroxyl, alkyl, haloalkyl, benzyl, benzoyl, alkoxy, carboxyl, amido, amino, and alkylamino. Examples of such groups are N,N-diethylamino, N-benzoylamino, N-methoxyamino, N-carboethoxyamino, and N-chloroethylamino. Also, both the substituents on the amino group can be combined together to form 5 or 6-membered cyclic ring system which may be represented by pyrrolidino, piperidino, piperizino, morphilino, imidazolino, or thiazolidino.

Examples of 3 to 8 membered cyclic ring systems containing carbon and optionally containing one or two heteroatoms selected from oxygen, sulfur and nitrogen are piperidine and pyrrolidine.

In our copending application Ser. No. 08/771,391, we have described and claimed the compounds of the formula 12,

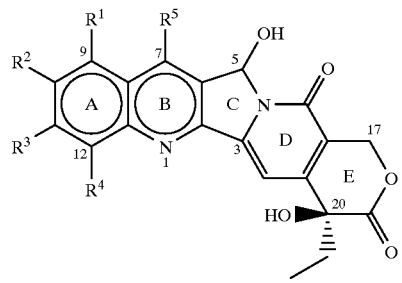

and the process for their preparation.

Employing the compounds of the formula 12, we have prepared the compounds of the formula 1 as described in the present invention.

Accordingly the present invention provides a process for the preparation of the compounds of the formula 1,

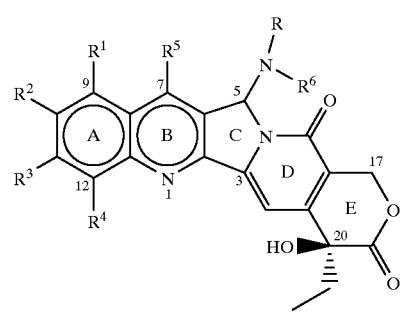

wherein $R^1$, $R^2$, $R^3$ and $R^4$ are independently the same or different and represent hydrogen, hydroxy, lower alkoxy, aryloxy, lower alkanoyl, nitro, cyano, halo, carboxy, carbonyloxy, amino, substituted amino, lower alkyl, substituted lower alkyl or $R^2$, $R^3$ combined together represent —O—$(CH_2)_n$—O— where n=1 or 2; $R^5$ represents hydrogen, lower alkyl, substituted lower alkyl, lower aralkyl, hydroxymethyl, carboxymethyl, aminomethyl, substituted aminomethyl where the amino group can be mono or disubstituted in which both substituents are independent or combined together to form a 5–6 membered cyclic ring system containing carbon and optionally containing one or two heteroatoms selected from oxygen, nitrogen or sulfur; wherein 5–6 is the number of atoms in the cyclic ring system and R represents hydrogen, lower alkyl, lower alkenyl, lower alkanoyl, substituted lower alkyl, substituted lower alkenyl, substituted lower alkanoyl, phenyl, benzyl or benzoyl in which the phenyl group may be unsubstituted or substituted; or lower alkoxycarbonyl and $R^6$ represents hydrogen, hydroxy, lower alkoxy, COOR' where R' represents hydrogen, lower alkyl, lower aralkyl; $R^6$ may also represent amide or amino group in which the amino group can be unsubstituted or mono, or disubstituted in which both substituents are independent or combined together to form a cyclic ring system of 3 or 8 atoms containing carbon, and optionally containing one or more heteroatoms selected from nitrogen, oxygen or sulfur; phenoxy, phenyl, benzoyl or benzyl where the phenyl group can be unsubstituted or substituted with mono, di or trisubstituents which may be selected from halogen, hydroxy, lower alkoxy, cyano, carboxy, nitro, amido, amino, substituted amino, lower alkyl, substituted lower alkyl; cycloalkyl or cycloalkyl lower alkyl where the cyclic ring is in the range of 3 membered to 7 membered ring system containing all carbon atoms; lower alkyl groups substituted with heterocyclic rings where the heterocyclic ring system has 3 to 7 atoms, said ring system containing carbon with at least one heteroatom such as oxygen, nitrogen, or sulfur, the number of atoms in the heterocyclic ring system being 3 or 7; lower alkanoyl, lower alkyl, substituted lower alkyl where the substiuents can be halogen, hydroxy, alkoxy, aryloxy, carboxyl, cyano, thio, thioalkyl, thioaryl, aryl, heteroaryl, nitro, amido or amino in which the amino group can be unsubstituted, mono, or disubstituted in which both substituents are independent or combined together to form a cyclic ring system of 5 to 8 atoms containing carbon and optionally containing one or more heteroatoms selected from nitrogen, oxygen or sulfur, which comprises, (i) reacting the compounds of the formula 12,

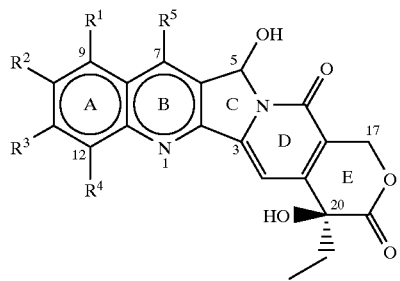

12 where $R^1$ through $R^5$ have the meaning described above, in the presence of a base, with a compound having the formula $R^6$—$NH_2$ to obtain compounds of the formula 13,

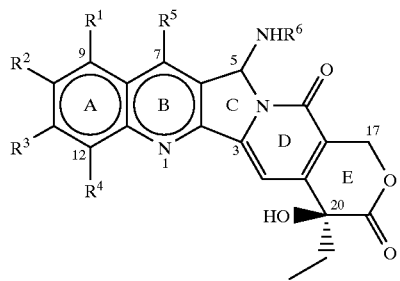

13 wherein $R^1$, $R^2$, $R^3$, $R^4$, $R^5$, and $R^6$ have the meaning described above, (ii) reacting the compounds of the formula 13, in the presence of a base, with a reagent having the formula R—G where G represents halogen to obtain compounds of the formula 1

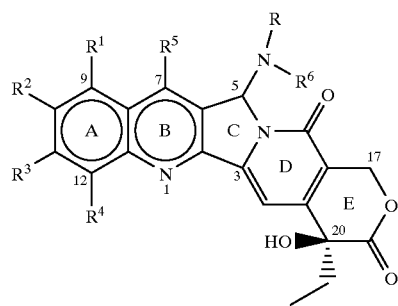

1 where R represents lower alkyl, phenyl, benzyl or benzoyl in which the phenyl group may be unsubstituted or substituted; lower alkoxycarbonyl, lower alkenyl, substituted lower alkenyl, substituted lower alkyl, lower alkanoyl, or substituted lower alkanoyl and $R^1$ through $R^6$ have the meaning described above.

Accordingly, this is the first time a process for the preparation of C-5 N-substituted camptothecin derivatives of the formula 1, starting from the compounds of formula 12 using a semi-synthetic approach has been developed. The compounds of the formula 1 prepared by the process of the present invention thus represents diastereomers containing the newly created C-5 chiral center. Indeed, the compounds of the general formula 1 are isolated as a mixture of 20(S),5(R) and 20(S),5(S) diastereomers. However, by the application of conventional analytical techniques, the two diastereomers have also been separated into their single optically pure entities.

According to the process of the present invention, the compounds of the formula 12 were reacted with compounds of the general formula $R^6$—$NH_2$, where $R^6$ has the meaning mentioned above, in the presence of a base to afford compounds of the formula 13. The bases employed in this reaction sequence can be selected from inorganic or organic bases such as sodium bicarbonate, potassium carbonate, sodium hydride, potassium hydride, pyridine, piperdine, triethylamine, diisopropylamine, pyrrolidine, or dimethylaminopyridine. The solvents used in the reaction can be selected from methanol, ethanol, benzene, toluene, N,N-dimethylformamide, chloroform, or dichloroethane. The reaction can be effected at a temperature in the range of 40–140° C. To obtain the compounds of the formula 1 where the C-5 substitution is a disubstituted amino group such as $NRR^6$, compounds of the formula 13 were reacted with reagents having the formula R—G where G denotes halogen and R represents lower alkyl, phenyl, benzyl or benzoyl in which the phenyl group may be unsubstituted or substituted; lower alkoxycarbonyl, lower alkanoyl, substituted lower alkanoyl; lower alkenyl; substituted lower alkyl; or substituted lower alkenyl in the presence of a base. The base used in the reaction can be selected from sodium carbonate, sodium bicarbonate, potassium carbonate, barium carbonate, lithium carbonate, pyridine, piperidine, triethylamine, diisopropylamine or 4-N,N-dimethylaminopyridine. The solvent used in the reaction can be chosen from dichloromethane, chloroform, benzene, toluene, tetrahydrofuran, ethyl acetate or a combination of these solvents. The reaction temperature can be in the range of 0C. to 100° C., preferably in the range of 0° C. to 60° C.

Thus, the present invention is of particular significance in developing 5-N-substituted 20(S)-camptothecin derivatives as a new class of C-ring modified camptothecin analogues which are useful as anti-tumor and/or anti-viral agents. The present invention is also of particular significance as the process developed and described here is highly versatile and amenable for large scale preparation of these camptothecin derivatives having the general formula 1.

The methodology developed and described in the present invention will provide access to a wide variety of C-5 substituted C-ring analogues having diverse substituents on rings A and B of 20(S)-camptothecin. Some of the preferred compounds are those where $R^1$ is nitro, amino, aminoalkyl, hydroxy, or methoxy; $R^2$ is hydroxy, carbonyloxy or halo; $R^2$, $R^3$ combined together represent methylenedioxy or ethylenedioxy; $R^5$ is ethyl, aminomethyl or substituted aminomethyl; $R^6$ is hydroxy, methyl, 2'-hydroxyethyl, 4-hydroxybutyl, alkoxyethyl or aminoethyl where amino group may be dimethylamino, diethylamino, pyrrolidino, piperidino, morphilino, piperizino, or imidazolino; and R group may be methyl, allyl, benzyl, tert.butoxycarbonyl (Boc), benzoyl, p-fluoro benzoyl, p-chloro benzoyl, or p-tert.butyl benzoyl.

Representative of such examples are:
1) 5-Hydroxylamino CPT
2) 5-Hydroxyethylamino CPT
3) 5-Benzylamino CPT
4) 5-N,N-Dimethylaminoethylamino CPT
5) 5-(1',3'-Dihydroxypropylamino) CPT
6) 5-Chloroethylamino CPT
7) 5-(4'-Hydroxybutylamino) CPT
8) 9-Methoxy-5-(N,N-dimethylethylenediamino) CPT
9) 9-Methoxy-5-(1',2'-dihydroxypropylamino) CPT
10) 9-Methoxy-5-pyrrolidinoethylamino CPT
11) 9-Methoxy-5-(4'-hydroxybutylamino) CPT
12) 9-Methoxy-5-morphilinoethylamino CPT
13) 9-Methoxy-5-piperidinoethylamino CPT
14) 5-Piperidinoethylamino CPT
15) 5-Pyrrolidinoethylamino CPT
16) 5-Piperizinoethylamino CPT
17) 5-(N-Benzoyl-2'-hydroxyethylamino) CPT
18) 5-(N-tert.Butoxycarbonyloxy-2'-hydroxyethylamino) CPT
19) 5-Methylamino CPT
20) 5-Methylamino-10-hydroxy CPT
where CPT refers to 20(S)-camptothecin.

Most of the compounds prepared by the present invention have water solubility ranging from 1 mg to 15 mg per ml at 37° C. Compounds prepared in the present invention exhibited good in vitro anti-cancer activity towards various human tumor cell lines, according to the results obtained from 60 human tumor cell line assay performed at National Cancer Institute (NCI), Bethesda, Md., U.S.A.

The results shown in Tables 1 and 2 were obtained from conducting experiments according to U.S. National Cancer Institute (NCI) protocols as given below:

Each test compound was screened against a battery of 60 human cell lines obtained from eight organs. In a typical procedure, the cell suspensions that were diluted according to the particular cell type and the expected target cell density (5000–40,000 cells per well based on cell growth characteristics) were added into 96-well microtiter plates. Inoculates were allowed a preincubation period of 24 h at 37° C. for stabilization. Dilutions at twice the intended test concentrations were added at time zero in 100-µl aliquots to microtiter plate wells. Usually test compounds were evaluated at five 10-fold dilutions. The highest well concentration used in the test is $10^{-4}$ M. The cells are then incubated in the presence of drug (the test compound) for a further 48 h in 5% $CO_2$ atmosphere and 100% humidity. At the end of this time, the adherent cells are fixed to the plate by means of trichloroacetic acid, and after a number of washes, the cell layer is treated with the protein stain Sulforhodamine B. The optical density which is proportional to protein mass, is then read by automated spectrophotometric plate readers at a wavelength of 515 nm. Readings are transferred to a microcomputer and final reports are generated using especially developed software.

TABLE 1

| S. NO. | COMPOUND | IC50(µm)[a] |
|---|---|---|
| 1. | 5-Hydroxylamino CPT | 2.39 |
| 2. | 5-(2'-Hydroxyethylamino) CPT | >30 |
| 3. | 5-Benzylamino CPT | >30 |
| 4. | 5-(N,N-Dimethylethylenediamino) CPT | >30 |
| 5. | 9-Methoxy-(2',3'-dihydroxypropylamino) CPT | 6.60 |
| 6. | 9-Methoxy-5-(4'-hydroxybutylamino) CPT | 13.10 |
| 7. | 9-Methoxy-5-pyrrolidinoethylamino CPT | 31.6 |
| 8. | 9-Methoxy-5-piperidinoethylamino CPT | 28.10 |
| 9. | 9-Methoxy-5-morphilinoethylamino CPT | >30 |
| 10. | 10-Hydroxy-5-hydroxylamino CPT | 10.0 |
| 11. | 5-Methylamino CPT | 4.67 |
| 12. | 5-Pyrrolidinoethylamino CPT | >30 |
| 13. | 5-Piperidinoethylamino CPT | 23.4 |
| 14. | 5-Chloroethylamino CPT | 19.0 |
| 15. | 9-Methoxy-5-(N,N-dimethylethylenediamino) CPT | 9.54 |
| 16. | 9-Methoxy-5-(N,N-diethylpropylenediamino) CPT | 8.31 |
| 17. | 9-Methoxy-5-(N,N-diethylethylenediamino) CPT | 19.10 |

[a]IC50 = the mean value of the minimum drug concentration (µm) of the agent required to produce 50% cell growth inhibition (GI50) against NCI's 60 human tumor cell line assay.

TABLE 2

In vitro ANTI CANCER activity data of Examples 1, 11 and 12

| CELL PANEL | CELL LINE | EXAMPLE 12 | EXAMPLE 1 | EXAMPLE 11 |
|---|---|---|---|---|
| LEUKEMIA | | | | |
| | CCRF-CEM | 0.23 | — | — |
| | MOLT-4 | 0.15 | 0.18 | 0.01 |
| | HL 60 | 0.22 | 0.38 | 1.86 |
| | SR | 0.03 | 0.53 | 0.10 |
| NSLC | | | | |
| | H 460 | — | 0.48 | 1.54 |
| | HOP 62 | 1.73 | 0.38 | 7.41 |
| | H 522 | 2.88 | 0.20 | 5.37 |
| | H 23 | 2.57 | 1.62 | 4.16 |
| CNS | | | | |
| | SF-268 | 0.85 | — | 2.45 |
| | SF-539 | 1.81 | 1.20 | 3.16 |
| | SF 295 | 1.12 | 0.25 | 4.89 |
| RENAL | | | | |
| | 786-O | 4.07 | 0.56 | 2.69 |
| | ACHN | 0.97 | 0.40 | 3.16 |
| | CAKI-1 | 2.29 | — | 4.26 |
| MELANOMA | | | | |
| | LOX IMVI | 2.34 | 3.38 | 2.69 |
| | UACC 62 | — | 0.37 | 4.16 |
| | M-14 | 2.18 | 0.37 | 4.26 |
| | SK MEL-5 | 2.51 | 3.38 | 15 |

TABLE 2-continued

In vitro ANTI CANCER activity data of Examples 1, 11 and 12

| CELL PANEL | CELL LINE | EXAMPLE 12 | EXAMPLE 1 | EXAMPLE 11 |
|---|---|---|---|---|
| BREAST | | | | |
| | MCF-7 | 1.25 | 0.34 | 4.07 |
| | MCF7/ADR | 1.94 | 2.18 | >30 |
| | T 47D | 4.67 | 0.20 | 1.28 |

The data shown here refers to 50% Growth Inhibition (GI 50) values in μm concentraions.
NSLC refers to Non-Small Cell Lung cancer; CNS refers to Central Nervous System.

All of the compounds of the general formula 1 of the present invention, including the pharmaceutically acceptable salts thereof, and the compositions containing them, are useful as anti-cancer and anti-viral agents. Administration of the novel active compounds of the formula 1, in pure form or in an appropriate pharmaceutical composition can be carried out via any of the accepted modes of administration for serving similar utilities. Thus, administration can be, for example, orally, nasally, parenterally or topically, in the form of solid, semi-solid, lyophilized powder, or liquid dosage forms, such as for example, tablets, suppositories, pills, capsules, powders, solutions, suspensions, emulsions, creams, lotions, aerosols, ointments, injections or the like, preferably, in unit dosage forms suitable, for simple administration of precise dosages. The compositions will include a conventional pharmaceutical carrier, diluent or excipient and an active compound of general formula 1 and, in addition, may include either medicinal agents, pharmaceutical agents, diluents carriers, adjuvants, etc.

The invention is described in detail with specific examples given below which are provided by way of illustration only and should not be constructed to limit the scope of the invention.

EXAMPLES

Example 1

Preparation of 5-Hydroxylaminocamptothecin

A mixture of 5-hydroxycamptothecin of the formula 12 where $R^1=R^2=R^3=R^4=R^5=H$ (200 mg) and hydroxylamine hydrochloride (200 mg), were suspended in 30 ml of methanol and heated to reflux in the presence of pyridine (1 ml) for 20 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to obtain 140 mg of 5-hydroxylaminocamptothecin of the formula 13 $R^1=R^2=R^3=R^4=R^5=H$ and $R^6=OH$ as a white solid.; mp: 182° C.; $[\alpha]_D$ at 26° C.=+27.72 (c 0.101, $CHCl_3$); IR: 3745, 3400, 1744, 1654, 1602, 1156, 1046 $cm^{-1}$; Partial $^1H$ NMR data in ($CDCl_3$+DMSO-d6): δ 7.05 (br s. 1H, $D_2O$ exchangeable), 6.58(s, 0.5H), 6.49(s, 0.5H), 5.0 (br s, 1H, $D_2O$ exchangeable), 2.00–180(m, 2H), 1.15–0.95 (m, 3H); Mass (m/z): 361(M-OH), 348, 317, 218, 57.

Example 2

Preparation of 5-(2'Hydroxyethylamino) camptothecin

A mixture of 5-hydroxycamptothecin of the formula 12 where $R^1=R^2=R^3=R^4=R^5=H$ (200 mg) and 2-aminoethanol (60 mg) were suspended in 15 ml of methanol and heated to 70° C. in the presence of pyridine (1 ml) for 24 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to obtain 140 mg of 5-(2'-hydroxyethylamino)camptothecin of the formula 13 where $R^1=R^2=R^3=R^4=R^5=H$, $R^6=CH_2CH_2OH$ as a white solid.; mp: 130° C.; IR: 3331, 1745, 1656, 1590, 1404, 1158, 1103, 1044 $cm^{-1}$ Partial $^1H$ NMR (data in $CDCl_3$: δ 6.76 (s, 0.5H), 6.68 (s, 0.5H), 3.85(br s, 1H, $D_2O$ exchangeable), 3.51((br t, 2H), 2.51–2.38(m,1H), 2.28–2.15(m, 1H), 2.02–1.69(m, 2H), 1.06(t, J=7.5Hz, 1H); Mass (m/z): 409(M+1), 389, 361, 347, 319, 91, 57.

Example 3

Preparation of 5-(4'Hydroxybutylamino) camptothecin

A mixture of 5-hydroxycamptothecin of the formula 12 where $R^1=R^2=R^3=R^4=R^5=H$ (100 mg) and 4-aminobuthanol (50 mg) were suspended in 10 ml of methanol and heated to 65° C. in the presence of pyridine (0.5 ml) for 10 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to get 80 mg of 5-(4'-hydroxybutylamino)camptothecin of the formula 13 where $R^1=R^2=R^3=R^4=R^5=H$, $R^6=CH_2CH_2CH_2CH_2OH$ as a light yellow solid.; mp: 230° C.; IR: 3402, 1753, 1058, 1602, 1384, 1155, 1043 $cm^{-1}$;

Example 4

Preparation of 5-(N,N-Dimethylethylenediamino) camptothecin

A mixture of 5-hydroxycamptothecin of the formula 12 where $R^1=R^2=R^3=R^4=R^5=H$, (200 mg) and N,N-dimethylethylenediamine (100 mg) were suspended in 20 ml of methanol and heated to reflux in the presence of triethylamine (1 ml) for 8 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to get 145 mg of 5-(N,N-dimethylethylenediamino)camptothecin of the formula 13 where $R^1=R^2=R^3=R^4=R^5=H$, $R^6=CH_2CH_2NMe_2$ as a solid.; mp: 130° C.; $[\alpha]_D$ at 30° C.=+24.00(c 0.1, $CHCl_3$); IR: 3416, 1747, 1657, 1595, 1383, 1154, 1105, 1046 $cm^{-1}$; Partial $^1H$ NMR data in ($CDCl_3$+DMSO-d6): δ 6.72 (s, 0.5H), 6.65 (s, 0.5H), 5.66(d, J=16.5Hz, 0.5H), 5.64(d, J=16.5Hz, 0.5H), 5.28(d, J=16.5Hz, 0.5H), 5.26(d, J=16.5Hz, 0.5H), 5.49(br s, 1H, $D_2O$ exchangeable), 2.58–2.05(m,4H), 2.25(s,6H), 2.05–1.84(m,2H), 1.05(t, J=7.5Hz, 3H) ;Mass (m/z) : 436(M+1), 391, 363, 347, 303, 120, 85.

Example 5

Preparation of 5-Benzylaminocamptothecin

A mixture of 5-hydroxycamptothecin of the formula 12 where $R^1=R^2=R^3=R^4=R^5=H$ (100 mg) and benzylamine (40 mg) were suspended in 6 ml of methanol and heated to 75° C. in the presence of triethylamine (0.3 ml) for 10 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to get 60 mg of 5-benzylaminocamptothecin of the formula 13 where $R^1=R^2=R^3=R^4=R^5=H$, $R^6=CH_2Ph$ as a solid.; mp: 110° C.; IR: 3429, 1751, 1655, 1584, 1156, 1040 cm$^{-1}$; Partial $^1H$ NMR data in CDCl$_3$ δ 7.12–6.95(m, 5H), 6.75 (s, 0.5H), 6.68 (s, 0.5H), 5.64(d, J=16.5Hz, 0.5H), 5.54(d, J=16.5Hz, 0.5H), 5.24(d, J=16.5Hz, 0.5H), 5.14(d, J=16.5Hz, 0.5H), 4.05(br s, 1H, D$_2$O exchangeable), 3.75(s, 1H, D$_2$O exchangeable), 3.48–3.21( m, 2H), 2.00–1.79(m, 2H), 1.19–0.95(m, 3H); Mass (m/z) : 454(M+1), 378, 348, 106, 57.

Example 6

Preparation of 5-(2'Chloroethylamino)camptothecin

A mixture of 5-hydroxycamptothecin of the formula 12 where $R^1=R^2=R^3=R^4=R^5=H$, (50 mg) and 2-chloroethylamine (20 mg) were suspended in 6 ml of methanol and heated to reflux in the presence of triethylamine (1 ml) for 24 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to get 30 mg of 5-(2'-chloroethylamino)camptothecin of the formula 13 where $R^1=R^2=R^3=R^4=R^5=H$, $R^6=CH_2CH_2Cl$ as a solid.; mp: 170° C.; IR: 3422, 1746, 1657, 1600, 1226, 1155, 1046, 762 cm$^{-1}$; Partial $^1H$ NMR data in CDCl$_3$ δ 6.71(s, 0.5H), 6.65(s, 0.5H), 3.85(br s, 1H, D$_2$O exchangeable), 3.70(s, 1H, exchangeable), 3.70(s, 1H, D$_2$O exchangeable), 3.45(br t, 2H), 2.75–2.52(m, 1H), 2.45–2.22(m, 1H), 2.05–1.79(m, 2H), 1.18–0.99(m, 3H); Mass (m/z): 426(M+1), 390, 376, 347, 305, 79.

Example 7

Preparation of 5-(N,N-dimethylethylenediamo)-9-methoxycamptothecin

A mixture of 5-hydroxycamptothecin of the formula 12 where $R^1=OMe$, $R^2=R^3=R^4=R^5=H$ (100 mg) and N,N-dimethylethylenediamine (46 mg) were suspended in 25 ml of methanol and heated to reflux in the presence of triethylamine (1 ml) for 6 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using methanol-chloroform as an eluent to get 30 mg of 5-(N,N-Dimethylethylenediamino)-9-methoxycamptothecin of the formula 13 where $R^1=OMe$, $R^2=R^3=R^4=R^5=H$, $R^6=CH_2CH_2NMe_2$ as a solid.; mp: 85–87° C.; IR: 3412, 1743, 1665, 1583, 1260, 1167 cm$^{-1}$; $^1H$ NMR data in (CDCl$_3$+DMSO-d6): δ 8.87(s, 1H), 7.73(m, 3H), 7.56(s, 1H) 7.01(d, J=7.8Hz, 0.5H), 6.66(d, J=12Hz, 0.5H), 5.80(d, J=11Hz, 0.5H), 5.70(d, J=11Hz, 0.5H), 5.40(d, J=11Hz, 1H), 4.07(s, 3H), 3.32(br s, D$_2$O exchangeable), 2.56–1.82(m, 6H), 2.25(s, 6H), 2.30(1H, D$_2$O exchangeable), 1.04(m, 3H); Mass (m/z): 465(M+1), 439, 421, 392, 377, 333, 149, 125, 97.

Example 8

Preparation of 5-(1',3'-dihydroxypropyl-2'amino) camptothecin

A mixture of 5-hydroxycamptothecin of the formula 12 where $R^1=R^2=R^3=R^4=R^5=H$ (100 mg) and serinol (60 mg) were suspended in 10 ml of methanol and heated to reflux in the presence of triethylamine (0.5 ml) for 16 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to get 75 mg of 5-(1',3'-dihydroxypropyl-2'-amino) camptothecin of the formula 13 where $R^1=R^2=R^3=R^4=R^5=H$, $R^6=CH(CH_2OH)CH_2OH$ as a solid.; mp: 240° C.; IR: 3361, 1751, 1658, 1595, 1225, 1048 cm$^{-1}$; Partial $^1H$ NMR data in (CDCl$_3$ +DMSO-d6) δ 6.75(s, 0.5H), 6.65(s, 0.5H), 6.02(s, 1H, D$_2$O exchangeable), 4.25–4.05(m, 2H, D$_2$O exchangeable), 3.49–3.22(m, 4H) 2.78–2.58(m, 2H), 2.05–1.85 (m, 2H), 1.01 (t, J=7.5Hz, 3H); Mass (m/z): 419(M—H$_2$O), 406, 375, 362, 347, 90.

Example 9

Preparation of 5-(1',2'-Dihydroxypropylamino)-9-methoxycamptothecin

A mixture of 5-hydroxy-9-methoxycamptothecin of the formula 12 where $R^1=OMe$, $R^2=R^3=R^4=R^5=H$ (100 mg) and 3-amino-1,2-dihydroxypropane (46 mg) were suspended in 20 ml of methanol and heated to reflux in the presence of pyridine (0.5 ml) for 20 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using methanol-chloroform as an eluent to get 40 mg of 5-(1',2'-dihydroxypropylamino)-9-methoxycamptothecin of the formula 13 where $R^1=OMe$, $R^2=R^3=R^4=R^5=H$, $R^6=CH_2CHOHCH_2OH$ as a solid.; mp: 141° C.; $[α]_D$ at 28° C.=+29.04 (c 0.21, MeOH); IR: 3418, 1739, 1658, 1616, 1592, 1365, 1263, 1152, 1043, 830 cm$^{-1}$; Partial $^1H$ NMR data in (CDCl3+DMSO-d6): δ 6.99(t, J=8.7Hz, 0.5H), 6.55 (d, J=14.6Hz, 0.5H), 5.80(s, 1H, D$_2$O exchangeable), 5.62 (d, J=16Hz, 1H), 5.26(d, J=16Hz, 1H), 4.20(s, 1H, D$_2$O exchangeable), 4.06(s, 3H), 3.60(m, 1H), 3.45 (m,2H), 3.30 (m,2H), 1.96(2H), 1.01(m,3H); Mass (m/z): 468(M+1) 449, 424, 377, 333, 223, 149, 113, 8390.

Example 10

Preparation of 5-(4'Hydroxybutylamino)-9-methoxycamptothecin

A mixture of 5-hydroxy-9-methoxycamptothecin of the formula 12 where $R^1=OMe$, $R^2=R^3=R^4=R^5=H$, (100 mg) and 4-aminobutanol (42 mg) were suspended in 20 ml of methanol and heated to reflux in the presence of pyridine (0.4 ml) for 15 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using methanol-chloroform as an eluent to get 48 mg of 5-(4'-hydroxy butylamino)-9-methoxycamptothecin of the formula 13 where $R^1=OMe$, $R^2=R^3=R^4=R^5=H$, $R^6=CH_2CH_2CH_2CH_2OH$ as a solid.; mp: 182° C.; $[α]_D$ at 29° C.=+13.75 (c 0.08, MeOH); IR: 3357, 1748, 1653, 1599, 1462, 1365, 1267, 1187, 815 cm$^{-1}$; Partial $^1$H NMR data in (CDCl$_3$): δ 6.67(s, 0.5H), 6.61(s, 0.5H), 5.70(d, J=16Hz, 1H), 5.30 (d, J=16Hz, 1H), 4.06(s, 3H), 3.81(s, 1H, D$_2$O exchangeable), 3.50(m, 2H), 3.42(br s, 1H), D$_2$O exchangeable), 2.40–1.85(m, 4H), 1.55–1.35(m, 4H), 1.04 (m, 3H) ; Mass (m/z): 465(M+1) 378, 334, 319, 249, 205, 169, 97, 91.

Example 11

Preparation of 10-Hydroxy-5-hydroxylaminocamptothecin

A mixture of 10,5-dihydroxycamptothecin of the formula 12 where R$^2$=OH, R$^1$=R$^3$=R$^4$=R$^5$=H, (50 mg) and hydroxylamine hydrochloride (50 mg) were suspended in 10 ml of methanol and heated to reflux in the presence of pyridine (0.5 ml) for 18 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to get 35 mg of 10-Hydroxy-5-hydroxylaminocamptothecin of the formula 1 where R=R$^1$=R$^3$=R$^4$=R$^5$=H, R$^2$=R$^6$OH as a solid.; mp: 198° C.; IR: 3170, 1744, 1655, 1579, 1505, 1237, 1155, 1043, 833 cm$^{-1}$; $^1$H NMR (CDCl3+DMSO-6): δ 9.05(br s, 1H, D$_2$O) exchangeable) 8.35(s, 1H), 8.02(d, J=9Hz, 1H), 7.68 (s, 1H), 7.46(d, J=9Hz, 1H) 7.25(s, 1H), 6.52(s, 0.5H), 6.50(s, 0.5H), 5.58(d, J=16Hz, 1H), 5.23(d, J=16Hz, 1H), 3.85(br s, 2H, D$_2$O exchangeable), 1.97(m, 2H), 1.05(t, J=7Hz, 3H); Mass (m/z) 3785(M+1) 363, 336, 334, 318, 290, 278, 248, 191, 149, 83.

Example 12

Preparation of 5-Methylaminocamptothecin

A mixture of 5-hydroxycamptothecin of the formula 12 where R$^1$=R$^3$=R$^4$=R$^5$=H, (100 mg) and 40% aqueous methylamine (0.2 ml) were dissolved in 10 ml of methanol and heated to 65° C. for for 16 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using ethylacetate-chloroform as an eluent to get 75 mg of 5-methylaminocamptothecin of the formula 13 where R$^1$=R$^3$=R$^4$=R$^5$=H, R$^6$=CH$_3$ as a solid.; mp: 142° C.; IR: 3360, 2925, 1746, 1656, 1594, 1460, 762 cm$^{-1}$; $^1$H NMR (CDCl$_3$): δ 8.42(s, 1H) 8.28(d, J=11.3Hz, 0.5H), 8.26(d, J=11.3z, 0.5H), 7.96 (d, J=11.3Hz, 1H), 7.82(t, J=6.8Hz, 1H) 7.68(t, J=6.8H, 1H)), 7.62(s, 1H), 6.71(s, 0.5H), 6.62(s, 0.5H), 5.72(d, J=16Hz, 1H), 5.28(d J=16Hz, 1H), 3.95 (br s, 1H, D$_2$O exchangeable), 2.82 (br s, 1H, D$_2$O exchangeable), 1.98(s, 3H), 1.94(m,2H), 1.05(t, J=7Hz, 3H); Mass (m/z): 377(M+1) 362, 348, 333, 304, 247, 218, 169, 95.

Example 13

Preparation of 5-(N-Benzoyl,N-2'-hydroxyethylamino)camptothecin

Step 1: 5-(2'-Hydroxyethylamino)camptothecin of the formula 13 where R$^1$=R$^2$=R$^3$=R$^4$=R$^5$=H, R$^6$=CH$_2$CH$_2$OH was prepared as described in example 2.

Step 2: To a solution of 100 mg of 5-(2'-Hydroxyethylamino)camptothecin of the formula 13 where R$^1$=R$^2$=R$^3$=R$^4$=R$^5$=H, R$^6$=CH$_2$CH$_2$OH in 10 ml of ethyl acetate, 5 ml of saturated sodium bicarbonate solution was added followed by 1.2 equiv. of benzoyl chloride and the reaction mixture was stirred at 25° C. for 2 h. Reaction mixture was poured into ice water and extracted with ethyl acetate. Evaporation of organic layer and purification of the resulting residue over silica gel column afforded 64 mg of 5-(N-benzoyl,N-2'-hydroxyethylamino)camptothecin of the formula 1 where R$^1$=R$^1$=R$^3$=R$^4$=R$^5$=H, R$^6$=CH$_2$CH$_2$OH, R=COPh; IR: 3382, 1747, 1662, 1620, 1400, 1227, 1156, 1050, 713 cm$^{-1}$; $^1$H NMR (CDCl$_3$): δ 8.50(s, 1H) 8.28(d, J=8Hz, 1H), 8.05(d, J=8Hz, 1H), 8.00–7.24(m, 8H), 7.00(s, 0.5H), 6.85(s, 0.5H), 5.72(d, J=16Hz, 1H), 5.28(d, J=16Hz, 1H), 4.35–2.91(m, 4H), 3.85(br s, D$_2$O exchangeable, IH), 2.15–1.79 (m,2H), 1.07(t, J=7Hz, 3H), Mass (m/z): 512(M+1) 469, 424, 406, 389, 363, 347, 303, 275, 219, 122, 105, 96.

Example 14

Preparation of 5-(N-tert.Butoxycarbonyl, N-2'hydroxyethylamino)camptothecin

Step 1: 5-(2'-Hydroxyethylamino)camptothecin of the formula 13 where R$^1$=R$^2$=R$^3$=R$^4$=R$^5$=H, R$^6$=CH$_2$CH$_2$OH was prepared as described in example 2.

Step 2: To a solution of 50 mg of 5-(2'-Hydroxyethylamino)camptothecin of the formula 13 where R$^1$=R$^2$=R$^3$=R$^4$=R$^5$=H, R$^6$=CH$_2$CH$_2$OH in 8 ml of ethyl acetate, 20 mg of saturated sodim bicarbonate solution was added followed by 1.2 equiv. of di-tert.butyl dicarbonate and the reaction mixture was stirred at 25° C. for 3 h. Reaction mixture was poured into ice water and extracted with ethyl acetate. Evaporation of organic layer and purification of the resulting residue over silica gel column afforded 64 mg of 17-(N-tert.butoxycarbony,N-2'-hydroxyethylamino) camptothecin of the formula 1 where R$^1$=R$^2$=R$^3$=R$^4$=R$^5$=H, R$^6$=CH$_2$CH$_2$OH, R=OCOBu$^t$.

Example 15

Preparation of 5-(Pyrrolidinoethylamino) camptothecin

A mixture of 5-hydroxy camptothecin of the formula 12 where R$^1$=R$^2$=R$^3$=R$^4$=R$^5$=H, (100 mg) and pyrrolidinoethylamine (42 mg) were suspended in 15 ml of methanol and heated to reflux in the presence of pyridine (0.4 ml) for 18 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using methanol-chloroform as an eluent to get 48 mg of 5-(pyrrolidinoethylamino) camptothecin of the formula 13 where R$^1$=R$^2$=R$^3$=R$^4$=R$^5$=H, R$^6$=CH$_2$CH$_2$N(CH$_2$)$_4$ as a solid.; mp: 130° C.; $^1$H NMR (CDCl$_3$): δ 8.50 (s, 1H) 8.28(d, J=8Hz, 1H), 7.95(d, J=8Hz, 1H), 7.85 (t, J=8Hz, 1H), 7.73–7.55(m, 2H), 6.72(s, 0.5H), 6.62(s, 0.5H), 5.75( d, J=16Hz, 0.5H), 5.65(d, J=16Hz, 0.5H), 5.35(d, J=16Hz, 0.5H), 5.25(d, J=16Hz, 0.5H), 3.85 (br s, D$_2$O exchangeable, 1H)), 2.69–1.58(m,14H), 1.07(t, J=7Hz, 3H);

Example 16

Preparation of 5-(Piperidinoethylamino) camptothecin

A mixture of 5-hydroxy camptothecin of the formula 12 where R$^1$=R$^2$=R$^3$=R$^4$=R$^5$=H, (250 mg) and piperidinoethylamine (100 mg) were suspended in 25 ml of methanol and heated to reflux in the presence of pyridine (0.8 ml) for 18 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using methanol-chloroform as an eluent to get 220 mg of 5-(piperidinoethylamino) camptothecin of the formula 13 where $R^1=R^2=R^3=R^4=R^5=H$, $R^6=CH_2CH_2N(CH_2)_5$ as a solid.; mp: 202° C.; $^1H$ NMR (CDCl$_3$): δ 8.50 (s, 1H) 8.28(d, J=8Hz, 1H), 7.95(d, J=8Hz, 1H), 7.85 (t, J=8Hz, 1H), 7.73–7.55(m, 2H), 6.75(s, 0.5H), 6.65(s, 0.5H), 5.75(d, J=16Hz, 0.5H), 5.65(d, J=16Hz, 0.5H), 5.35(d, J=16Hz, 0.5H), 5.25(d, J=16Hz, 0.5H), 3.85 (br s, D$_2$O exchangeable, 1H)), 2.50–1.79(m,10H), 1.62–1.31(m,6H), 1.07(t, J=7Hz, 3H);

Example 17

Preparation of 5-(2'-Methoxyethylamino) camptothecin

A mixture of 5-hydroxy camptothecin of the formula 12 where $R^1=R^2=R^3=R^4=R^5=H$ (150 mg) and 2'-methoxyethylamine (73 mg) were suspended in 20 ml of methanol and heated to reflux in the presence of pyridine (0.6 ml) for 18 h. Reaction mixture was concentrated to dryness and the residue was extracted with ethylacetate. Organic layer was washed with brine and dried over anh. sodium sulfate. Evaporation of the solvent furnished an oily residue which was purified over silica gel column using acetone-chloroform as an eluent to get 98 mg of 5-(2'-methoxyethylamino)camptothecin of the formula 13 where $R^1=R^2=R^3=R^4=R^5=H$, $R^6=CH_2CH_2OMe$ as a solid.; mp: 78° C.; IR: 3345, 2927, 1748, 1656, 1593, 1155, 1042, 761 cm$^{-1}$; $^1H$ NMR (CDCl$_3$): δ 8.50(s, 1H) 8.28 (d, J=8Hz, 1 H), 7.95(d, J=8Hz, 1H), 7.85 (t, J=8Hz, 1H), 7.73–7.55 (m, 2H), 6.65(s, 0.5H), 6.60(s, 0.5H), 5.72(d, J=16Hz, 1H), 5.28 (d, J=16Hz, 1H), 3.7(s, D$_2$O exchangeable, 1H), 3.42–3.28(m, 2H), 3.19(s,3H), 2.35–1.79(m,4H), 1.07(t, J=7Hz, 3H); Mass(m/z): 435(M+1), 348, 332, 319, 304, 275, 247, 218, 191, 167, 88.

Example 18

Preparation of 5-(N,N-Dimethylamino)camptothecin

Step 1: 5-(N-Methylamino)camptothecin of the formula 13 where $R^1=R^2=R^3=R^4=R^5=H$, $R^6=Me$ was prepared as described in example 2.

Step 2: To a solution of 100 mg of 5-(N-methylamino) camptothecin of the formula 13 where $R^1=R^2=R^3=R^4=R^5=H$, $R^6=Me$ in 10 ml of ethyl acetate, 250 ml of anh.potassium carbonate was added followed by 1.2 equiv. of methyl iodide and the reaction mixture heated at 65° C. for 10 h. Acetone was removed and the residue was diluted with ethylacetate and washed with water and brine solution. Evaporation of organic layer and purification of the resulting residue over silica gel column afforded 60 mg of 5-(N,N-dimethylamino) camptothecin of the formula 1 where $R^1=R^2=R^3=R^4=R^5=H$, $R^6=R=Me$.

We claim:
1. A compound of the formula 1,

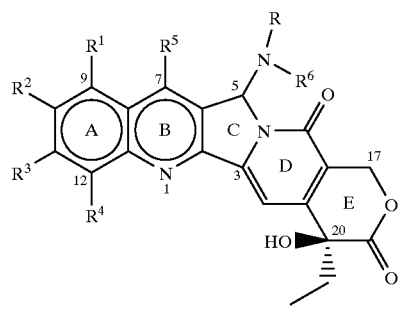

wherein $R^1$, $R^2$, $R^3$ and $R^4$ are independently the same or different and represent hydrogen, hydroxy, lower alkoxy, aryloxy, lower alkanoyl, nitro, cyano, halo, carboxy, carbonyloxy, amino, substituted amino, lower alkyl, substituted lower alkyl or $R^2$ and $R^3$ combined together represent —O—(CH$_2$)$_n$—O— where n=1 or 2; $R^5$ represents hydrogen, lower alkyl, substituted lower alkyl, lower aralkyl, hydroxymethyl, carboxymethyl, aminomethyl, substituted aminomethyl where the amino group is mono or disubstituted in which both substituents are independent or together with the linking nitrogen atom form a saturated 5 or 6 membered heterocyclic group of the formula (A)

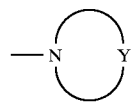

where Y represents O, S or NH; R represents hydrogen, lower alkyl, lower alkenyl, lower alkanoyl, substituted lower alkyl, substituted lower alkanoyl, substituted lower alkenyl, lower alkoxycarbonyl, phenyl, benzyl or benzoyl in which the phenyl group may be unsubstituted or substituted; $R^6$ represents hydrogen, hydroxy, lower alkoxy, or COOR' where R' represents hydrogen, lower alkyl or lower aralkyl; or $R^6$ represents amide or amino group in which the amino group can be unsubstituted, or mono, or disubstituted in which both substituents are independent or together with the linking nitrogen atom form a saturated 5 to 7 membered heterocyclic group of the formula (A)

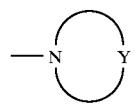

where Y represents CH$_2$, O, S or NH; phenoxy, phenyl, benzoyl or benzyl where the phenyl group can be unsubstituted or substituted with mono, di or trisubstitutents selected from halogen, hydroxy, lower alkoxy, cyano, carboxy, nitro, amido, amino or substituted amino, lower alkyl, substituted lower alkyl; cycloalkyl or cycloalkyl lower alkyl where the cyclic ring is a 3 membered to 7 membered ring system containing all carbon atoms; lower alkyl substituted with saturated 5 to 7 membered heterocyclic ring of the formula (B)

(B)

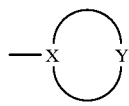

where X represents CH or N and Y represents O, S or NH; lower alkanoyl; lower alkyl; substituted lower alkyl where the substituents are selected from halogen, hydroxy, alkoxy, aryloxy, carboxyl, cyano, thio, thioalkyl, thioaryl, aryl, heteroaryl, nitro, amido or amino in which amino group can be unsubstituted, mono, or disubstituted in which both substituents are independent or together with the linking nitrogen atom form a saturated 5 to 7 membered heterocyclic group of the formula (A)

(A)

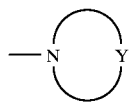

where Y represent $CH_2$, O, S or NH.

2. A compound of formula 13,

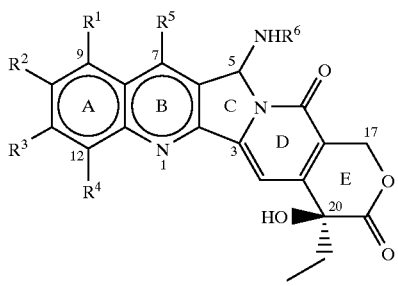

where $R^2$, $R^3$, $R^4$ and $R^5$ represent hydrogen, $R^1$ represents methoxy and $R^6$ represents 4'-hydroxybutyl.

3. A compound of formula 13,

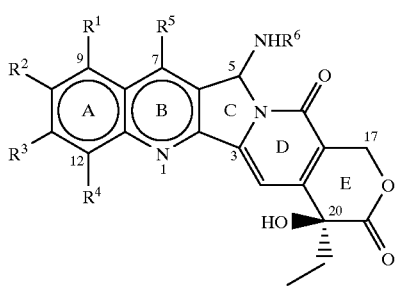

where $R^1$, $R^2$, $R^3$, $R^4$ and $R^5$ represent hydrogen, and $R^6$ represents hydroxyl.

4. A compound of formula 13,

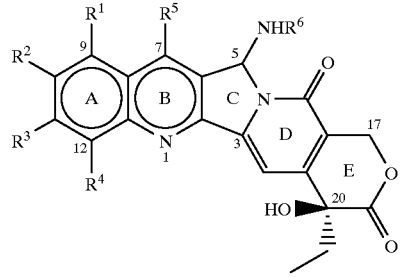

where $R^1$, $R^2$, $R^3$, $R^4$ and $R^5$ represent hydrogen, and $R^6$ represents methyl.

5. A compound of formula 13,

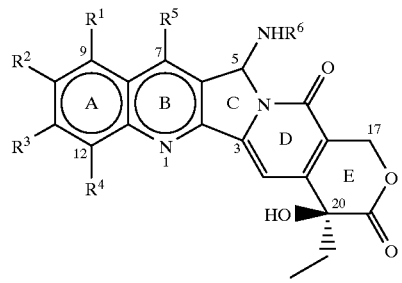

where $R^1$, $R^2$, $R^3$, $R^4$ and $R^5$ represent hydrogen, $R^2$ represents hydroxy, and $R^6$ represents methyl.

6. A compound of formula 1,

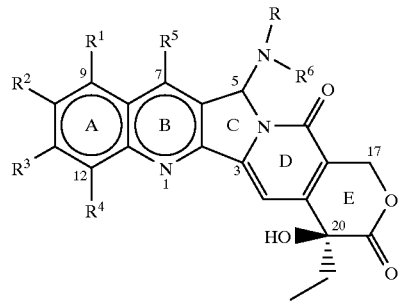

where $R^1$, $R^2$, $R^3$, $R^4$ and $R^5$ represent hydrogen, and R and $R^6$ represent methyl.

7. A compound of formula 1,

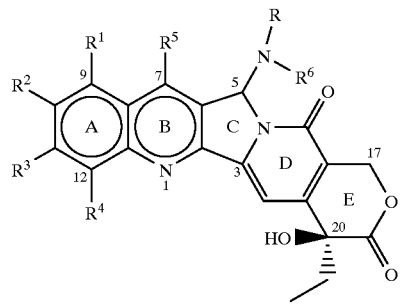

where $R^1$, $R^2$, $R^3$, $R^4$ and $R^5$ represent hydrogen, $R^6$ represents hydroxyl and R represents methyl.

8. A compound of formula 1

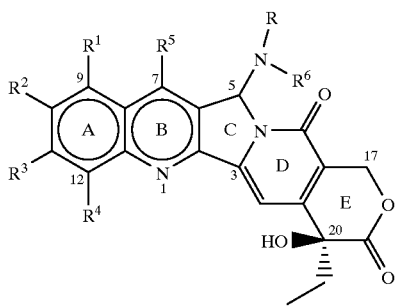

where $R^1$, $R^3$, $R^4$ and $R^5$ represent hydrogen, $R^2$ and $R^6$ represent hydroxyl and R represents methyl.

9. Compounds of formula 1 where R, $R^1$, $R^2$, $R^3$, $R^4$, $R^5$ and $R^6$ have the meaning described in claim 1 as a mixture of two diastereomers having 20(S), 5(R) and 20(S), 5(S) configurations.

10. A compound of formula 1 as claimed in claim 1 having 20(S), 5(R) configuration, substantially free from the 20(S), 5(S) stereoisomer, where R, $R^1$, $R^2$, $R^3$, $R^4$, $R^5$ and $R^6$ have the meaning described in claim 1.

11. A compound of formula 1 as claimed in claim 1 having 20(S), 5(S) configuration, substantially free from the 20(S), 5(R) stereoisomer, where R, $R^1$, $R^2$, $R^3$, $R^4$, $R^5$ and $R^6$ have the meaning described in claim 1.

12. A pharmaceutical composition comprising an effective amount of a compound of formula 1 as defined in claim 1 or a pharmaceutically acceptable salt thereof and a pharmaceutically acceptable non-toxic excipient, diluent or carrier.

13. A method for treating a cancer susceptible to campothecin treatment or leukemia comprising administering to a patient in need of said treatment an effective amount of a compound of formula 1 as defined in claim 1 or a pharmaceutically acceptable salt thereof.

14. A process for the preparation of a compound of the formula 1 as defined in claim 1 where R, $R^1$, $R^2$, $R^3$, $R^4$, $R^5$ and $R^6$ have the meaning described in claim 1 which comprises, (i) reacting a compound of formula 12,

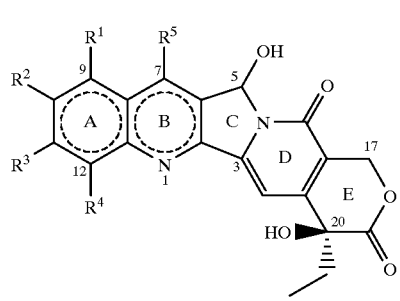

where $R^1$, $R^2$, $R^3$, $R^4$ and $R^5$ have the meaning described in claim 1, in the presence of a base, with a compound having the formula $R^6$—$NH_2$ to obtain a compound of formula 13,

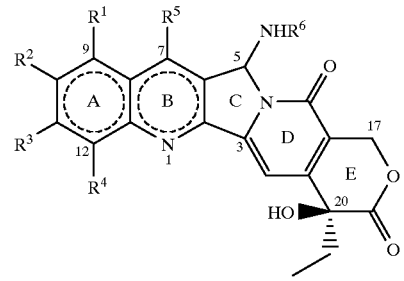

where $R^1$, $R^2$, $R^3$, $R^4$, and $R^5$ and $R^6$ have the meaning described in claim 1;

(ii) reacting a compound of formula 13, in the presence of a base, with a reagent having the formula R—G where R represents lower alkyl; lower alkenyl; substituted lower alkenyl; substituted lower alkyl; phenyl, benzyl or benzoyl in which the phenyl group may be unsubstituted or substituted; lower alkoxycarbonyl, lower alkanoyl or substituted lower alkanoyl and G represents halogen to obtain a compound of formula 1,

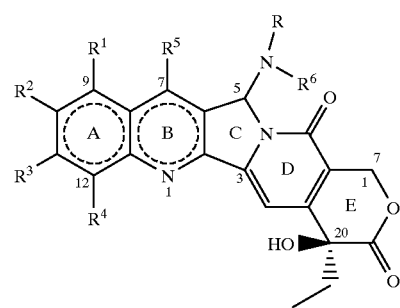

where $R^1$, $R^2$, $R^3$, $R^4$, $R^5$ and $R^6$ are defined in claim 1 and R is defined above.

15. A process for the preparation of compounds of formula 1 which comprises:

i) reacting the compounds of formula 12,

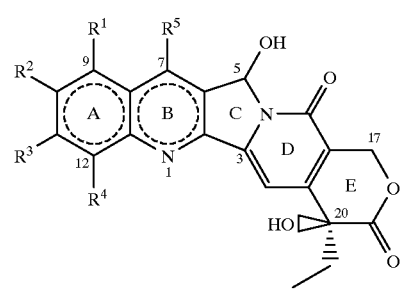

where $R^1$, $R^2$, $R^3$, $R^4$ and $R^5$ represent hydrogen, in the presence of pyridine, with hydroxylamine hydrochloride to obtain compounds of the formula 13, where $R^1$, $R^2$, $R^3$, $R^4$ and $R^5$ represent hydrogen and $R^6$ represents hydroxyl;

(ii) reacting the compounds of the formula 13 where $R^1$ through $R^6$ have the meaning described in step (i), in the presence of a potassium carbonate, with methyl iodide to obtain compound of formula 1,

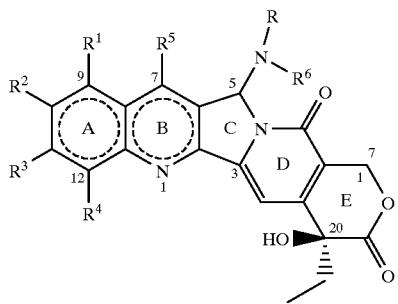

where R represents methyl $R^1$, $R^2$, $R^3$, $R^4$ and $R^5$ represents hydrogen and $R^6$ represents hydroxyl.

16. A compound according to claim 1 selected from the group consisting of:

5-Hydroxylamino CPT;
5-Hydroxyethylamino CPT;
5-Benzylamino CPT;
5-N,N-Dimethylaminoethylamino CPT;
5-(1',3'-Dihydroxypropylamino) CPT;
5-Chloroethylamino CPT;
5-(4'-Hydroxybutylamino) CPT;
9-Methoxy-5-(N,N-dimethylethylenediamino) CPT;
9-Methoxy-5-(1',2'-dihydroxypropylamino) CPT;
9-Methoxy-5-pyrrolidinoethylamino CPT;
9-Methoxy-5-(4'-hydroxybutylamino) CPT;
9-Methoxy-5-morphilinoethylamino CPT;
9-Methoxy-5-piperidinoethylamino CPT;
5-Piperidinoethylamino CPT;
5-Pyrrolidinoethylamino CPT;
5-Piperizinoethylamino CPT;
5-(N-Benzoyl-2'-hydroxyethylamino) CPT;
5-(N-tert. Butoxycarbonyloxy-2'-hydroxyethylamino) CPT;
5-Methylamino CPT and
5-Methylamino-10-hydroxy CPT
where CPT is 20(S)-camptothecin.

17. A compound according to claim 1 wherein the substituents of phenyl are selected from the group consisting of hydroxyl, lower alkyl, haloalkyl, phenyl, benzyl, halogen, lower alkoxy, thioalkoxy, benzyloxy, carboxyl, cyano, nitro, amido, amino and alkylamino.

18. A compound according to claim 1 wherein the substituents of alkyl are selected from the group consisting of hydroxyl, lower alkyl, haloalkyl, phenyl, benzyl, halogen, lower alkoxy, thioalkoxy, benzyloxy, carboxyl, cyano, nitro, amido, amino and alkylamino.

19. A compound according to claim 1 wherein the substituents of amino are selected from the group consisting of hydroxyl, lower alkyl, haloalkyl, benzyl, benzoyl, lower alkoxy, carboxyl, amido, amino, and alkylamino.

* * * * *

UNITED STATES PATENT AND TRADEMARK OFFICE

CERTIFICATE OF CORRECTION

PATENT NO. : 5,972,955
DATED : October 26, 1999
INVENTOR(S) : Subrahmanyam Duvvuri It is certified that error appears in the above-identified patent and that said Letters Patent is hereby corrected as shown below:

On the title page, Item [73] before "Dr."

Insert - -  REDDY-CHEMINOR, INC.,
            RIDGEWOOD, NEW JERSEY - -

Signed and Sealed this

Fourth Day of July, 2000

*Attest:*

Q. TODD DICKINSON

*Attesting Officer*   *Director of Patents and Trademarks*